United States Patent [19]
Goedeke et al.

[11] Patent Number: 5,843,139
[45] Date of Patent: Dec. 1, 1998

[54] ADAPTIVE, PERFORMANCE-OPTIMIZING COMMUNICATION SYSTEM FOR COMMUNICATING WITH AN IMPLANTED MEDICAL DEVICE

[75] Inventors: Steven D. Goedeke, Forest Lake; Gregory J. Haubrich, Champlin; John G. Keimel, New Brighton; David L. Thompson, Fridley, all of Minn.

[73] Assignee: Medtronic, Inc., Minneapolis, Minn.

[21] Appl. No.: 816,223

[22] Filed: Mar. 12, 1997

Related U.S. Application Data

[62] Division of Ser. No. 587,851, Jan. 11, 1996, Pat. No. 5,683,432.

[51] Int. Cl.[6] .................................................. A61N 1/08
[52] U.S. Cl. ............................... 607/32; 607/31; 607/60; 128/403
[58] Field of Search ................................ 607/60, 31, 32; 128/903

[56] References Cited

U.S. PATENT DOCUMENTS

| | | |
|---|---|---|
| 3,311,111 | 3/1967 | Bowers . |
| 3,518,997 | 7/1970 | Sessions . |
| 3,623,486 | 11/1971 | Berkovitz . |
| 3,631,860 | 1/1972 | Lopin . |
| 3,738,369 | 6/1973 | Adams . |
| 3,805,796 | 4/1974 | Terry, Jr. et al. . |
| 4,066,086 | 1/1978 | Alferness et al. . |
| 4,208,008 | 6/1980 | Smith . |
| 4,211,235 | 7/1980 | Keller, Jr. et al. . |
| 4,223,679 | 9/1980 | Schulman et al. . |
| 4,233,985 | 11/1980 | Hartlaub et al. . |
| 4,236,524 | 12/1980 | Powell et al. . |
| 4,250,884 | 2/1981 | Hartlaub et al. . |
| 4,253,466 | 3/1981 | Hartlaub et al. . |
| 4,273,132 | 6/1981 | Hartlaub et al. . |
| 4,273,133 | 6/1981 | Hartlaub et al. . |
| 4,374,382 | 2/1983 | Markowitz . |
| 4,401,120 | 8/1983 | Hartlaub et al. . |
| 4,520,825 | 6/1985 | Thompson et al. . |
| 4,531,523 | 7/1985 | Anderson . |
| 4,550,732 | 11/1985 | Batty, Jr. et al. . |
| 4,556,063 | 12/1985 | Thompson et al. . |
| 4,561,443 | 12/1985 | Hogrefe et al. ............................ 607/31 |
| 4,571,589 | 2/1986 | Slocum et al. . |
| 4,601,291 | 7/1986 | Boute et al. . |
| 4,676,248 | 6/1987 | Berntson . |
| 5,052,388 | 10/1991 | Sivula et al. . |
| 5,107,833 | 4/1992 | Barsness . |
| 5,127,404 | 7/1992 | Wyborney et al. . |
| 5,226,413 | 7/1993 | Bennett et al. . |
| 5,271,395 | 12/1993 | Wahlstrand et al. . |
| 5,324,315 | 6/1994 | Grevious . |
| 5,342,408 | 8/1994 | deCoriolis et al. . |
| 5,354,319 | 10/1994 | Wyborney et al. . |
| 5,466,246 | 11/1995 | Silvian . |
| 5,476,488 | 12/1995 | Morgan et al. . |
| 5,617,871 | 4/1997 | Burrows .................................... 607/32 |
| 5,718,234 | 2/1988 | Warden et al. . |

*Primary Examiner*—William E. Kamm
*Assistant Examiner*—Carl H. Layno
*Attorney, Agent, or Firm*—Reed A. Duthler; Harold R. Patton

[57] ABSTRACT

An adaptive, performance-optimizing communication system for communicating with an implanted medical device in which signals are transmitted and received in accordance with predetermined, interrelated operational parameters, such as transmission rate, transmitter power, and the like. Various aspects of system performance, including bit error rate in received signals, the strength of received signals, the signal-to-noise ratio of received signals, the presence of local RF noise and non-telemetry related RF signals, and the like, are dynamically monitored by the communication system, to determine whether predetermined system performance goals are being met. If it is determined that one or more system performance goals are not being met, one or more operational parameters may be automatically adjusted so that desired performance can be achieved.

4 Claims, 6 Drawing Sheets

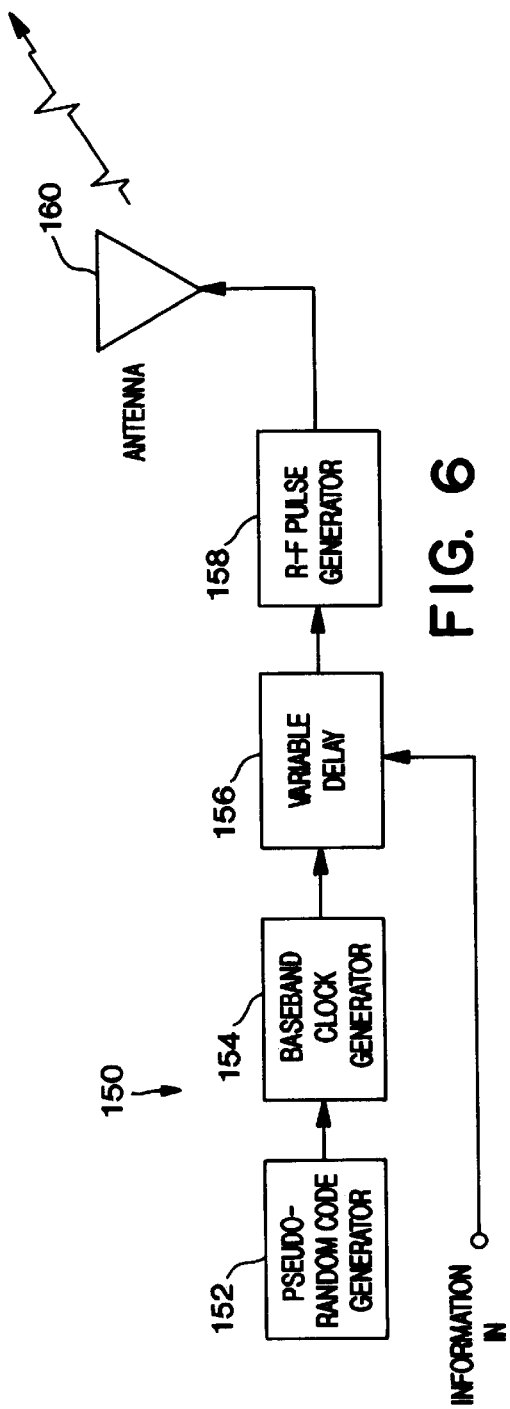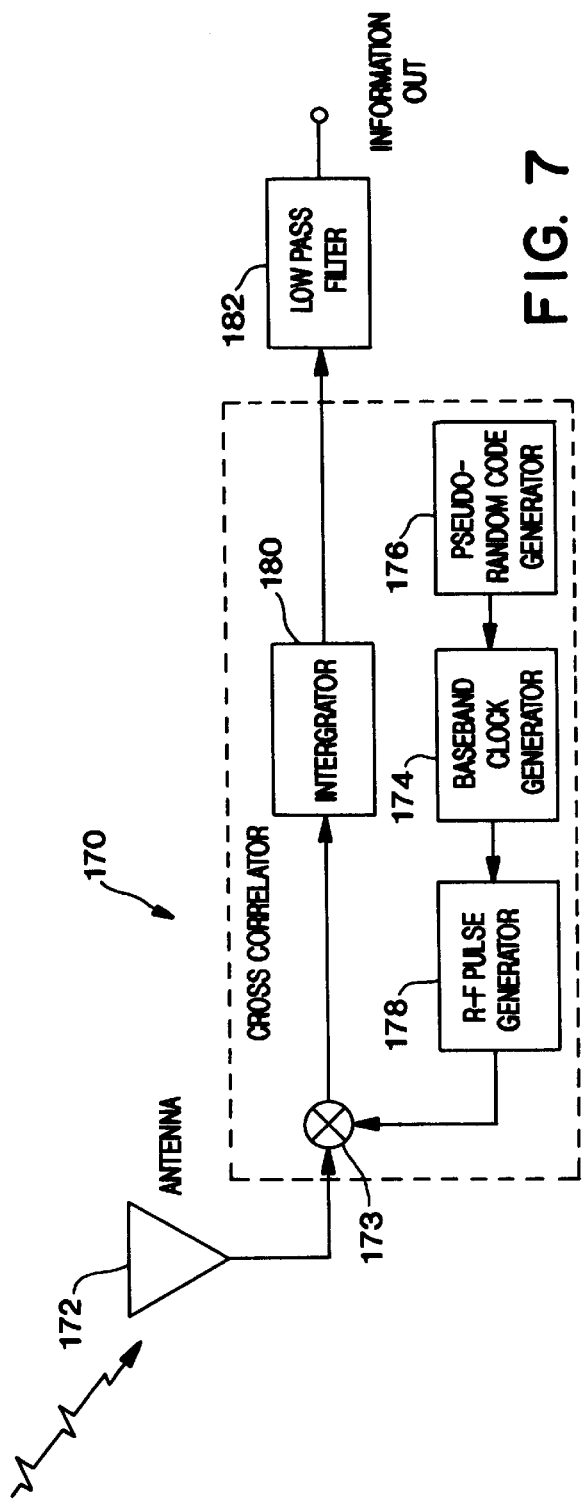

ADAPTIVE, PERFORMANCE-OPTIMIZING COMMUNICATION SYSTEM FOR COMMUNICATING WITH AN IMPLANTED MEDICAL DEVICE

This is a divisional of application Ser. No. 08/584,851 filed on Jan. 11, 1996, now U.S. Pat. No. 5,683,432, ISSUED Nov. 4, 1997.

FIELD OF THE INVENTION

This invention relates to the field of body-implantable medical devices, and more particularly relates to implantable medical devices which include a communication subsystem.

BACKGROUND OF THE INVENTION

Since the introduction of the first implantable pacemakers in the 1960's, there have been considerable advancements both in the field of electronics and the field of medicine, such that there is presently a wide assortment of commercially-available body-implantable electronic medical devices. The class of implantable medical devices now includes not only pacemakers, but also implantable cardioverters, defibrillators, neural stimulators, and drug administering devices, among others. Today's state-of-the-art implantable medical devices are vastly more sophisticated and complex than early ones, capable of performing significantly more complex tasks. The therapeutic benefits of such devices have been well-proven.

As the functional sophistication and complexity of implantable medical device systems have increased over the years, it has become increasingly more important for such systems to include a system for facilitating communication between one implanted device and another implanted device and/or an external device, for example, a programming console, monitoring system, or the like.

Shortly after the introduction of the earliest fixed-rate, non-inhibited pacemakers, it became apparent that it would be desirable for a physician to non-invasively obtain information regarding the operational status of the implanted device, and/or to exercise at least some amount of control over the device, e.g., to turn the device on or off or adjust the fixed pacing rate, after implant. Initially, communication between an implanted device and the external world was primarily indirect. For example, information about the operational status of an implanted device could be communicated via the electrocardiogram of the patient by modulating the rate of delivery of stimulating pulses in some manner. This was the case for the Medtronic Spectrax™, circa 1979, for which a 10% change in pacing rate was used to indicate battery status. This method could only provide a very low data rate transmission without interfering with the clinical application of the device. An early method for communicating information to an implanted device was through the provision of a magnetic reed switch in the implantable device. After implant, the reed switch would be actuated by placing a magnet over the implant site. Reed switch closure could then be used, for example, to alternately activate or deactivate the device. Alternatively, the fixed pacing rate of the device could be adjusted up or down by incremental amounts based upon the duration of reed switch closure.

Over time, many different schemes utilizing a reed switch to adjust parameters of implanted medical devices have been developed. See, for example, U.S. Pat. No. 3,311,111 to Bowers, U.S. Pat. No. 3,518,997 to Sessions, U.S. Pat. No. 3,623,486 to Berkovits, U.S. Pat. No. 3,631,860 to Lopin, U.S. Pat. No. 3,738,369 to Adams et al., U.S. Pat. No. 3,805,796 to Terry, Jr., and U.S. Pat. No. 4,066,086 to Alferness et al.

As new, more advanced features have been incorporated into implantable devices, it has been increasingly necessary to convey correspondingly more information to the device relating to the selection and control of those features. For example, if a pacemaker is selectively operable in various pacing modes (e.g., VVI, VDD, DDD, etc...), it is desirable that the physician or clinician be able to non-invasively select a mode of operation. Similarly, if the pacemaker is capable of pacing at various rates, or of delivering stimulating pulses of varying energy levels, it is desirable that the physician or clinician be able to select, on a patient-by-patient basis, appropriate values for such variable operational parameters.

Even greater demands are placed upon the communication system in implantable devices having such advanced features as rate adaptation based upon activity sensing, as disclosed, for example, in U.S. Pat. No. 5,052,388 to Sivula et al. entitled "Method and Apparatus for Implementing Activity Sensing in a Pulse Generator", or in U.S. Pat. No. 5,271,395 to Wahlstrand et al. entitled "Method and Apparatus for Rate-Responsive Cardiac Pacing." The Sivula et al. '388 and Wahlstrand et al. 395 patents are each hereby incorporated by reference herein in their respective entireties.

The information that is communicated to the implantable device in today's state-of-the-art pacemakers can include: pacing mode, multiple rate response settings, electrode polarity, maximum and minimum pacing rates, output energy (output pulse width and/or output current), sense amplifier sensitivity, refractory periods, calibration information, rate response attack (acceleration) and decay (deceleration), onset detection criteria, and perhaps many other parameter settings.

The need to be able to communicate more and more information to implanted devices (i.e., to establish "downlink" communication channels) quickly rendered the simple reed-switch closure arrangement inadequate. Also, it has become apparent that it would also be desirable not only to allow information to be communicated to the implanted device, but also to enable the implanted device to communicate information to the outside world (i.e., to establish "uplink" communication channels). (As used herein, the terms "uplink" and "uplink communication" will be used to denote the communications channel for conveying information from the implanted device to an external unit of some sort. Conversely, the terms "downlink" and "downlink communication" will be used to denote the communications channel for conveying information from an external unit to the implanted device. Although this terminology assumes that communication is occurring between an implanted device and an external device, it is contemplated that the communication system described herein is equally useful and beneficial in situations where communication occurs between any two or more devices, whether some are implanted and others are implanted, or all are implanted, or all are external.)

For diagnostic purposes, it is desirable for the implanted device to be able to communicate information regarding the device's operational status and the patient's condition to the physician or clinician. State of the art implantable devices are available which can even transmit a digitized electrical signal reflecting electrical cardiac activity (e.g., an ECG, EGM, or the like) for display, storage, and/or analysis by an external device. In addition, known pacemaker systems have been provided with what is referred to as Marker Channel™ functionality, in which uplink information regarding the pacemaker's operation and the occurrence of physiological events is communicated to an external programming unit. The Marker Channel™ information can then be printed or displayed in relation to an ECG so as to provide supplemental information regarding pacemaker operation. For example, events such as pacing or sensing of natural heartbeats are recorded with a mark indicating the time of the event relative to the ECG. This is helpful to the physician in interpreting the ECG, and in verifying proper operation of the pacemaker. One example of a Marker Channel™ system is disclosed in U.S. Pat. No. 4,374,382 to Markowitz, entitled "Marker Channel Telemetry System for a Medical Device." The Markowitz '382 patent is hereby incorporated by reference herein in its entirety.

Existing systems which provide a Marker Channel™ output operate basically by outputting an indication of a physiological or pacemaker event, e.g., a delivered stimulating pulse or a sensed heartbeat, at about the time of the event, thereby inherently providing the timing of the event in relation to the recorded ECG. Alternatively, the Marker Channel™ system can accumulate data over a period of time, e.g., one cardiac cycle, and transmit a batch of data for that interval at the beginning of the next interval. This is what appears to be proposed in U.S. Pat. No. 4,601,291 to Boute et al., entitled "Biomedical System with Improved Marker Channel Means and Method."

Various communication systems for providing the necessary uplink and downlink communications channels between an external unit and an implanted device have been shown in the art. Communication systems are disclosed, for example, in the following U.S. Patents: U.S. Pat. No. 4,539,992 to Calfee et al. entitled "Method and Apparatus for Communicating With Implanted Body Function Stimulator;" U.S. Pat. No. 4,550,732 to Batty Jr. et al. entitled "System and Process for Enabling a Predefined Function Within An Implanted Device;" U.S. Pat. No. 4,571,589 to Slocum et al. entitled "Biomedical Implant With High Speed, Low Power Two-Way Telemetry;" U.S. Pat. No. 4,676,248 to Berntson entitled "Circuit for Controlling a Receiver in an Implanted Device;" U.S. Pat. No. 5,127,404 to Wyborny et al. entitled "Telemetry Format for Implanted Medical Device;" U.S. Pat. No. 4,211,235 to Keller, Jr. et al. entitled "Programmer for Implanted Device;" the above-referenced Markowitz '382 patent; and U.S. Pat. No. 4,556,063 to Thompson et al. entitled "Telemetry System for a Medical Device." The Wyborny et al. '404 patent and the Thompson et al. '063 patent are hereby incorporated by reference herein in their respective entireties.

Typically, communication systems such as those described in the above-referenced patents are employed in conjunction with an external programming/processing unit. One programmer for non-invasively programming a cardiac pacemaker is described in its various aspects in the following U.S. Patents to Hartlaub et al., each commonly assigned to the assignee of the present invention and each incorporated by reference herein: U.S. Pat. No. 4,250,884 entitled "Apparatus For and Method Of Programming the Minimum Energy Threshold for Pacing Pulses to be Applied to a Patient's Heart"; U.S. Pat. No. 4,273,132 entitled "Digital Cardiac Pacemaker with Threshold Margin Check"; U.S. Pat. No. 4,273,133 entitled Programmable Digital Cardiac Pacemaker with Means to Override Effects of Reed Switch Closure"; U.S. Pat. No. 4,233,985 entitled "Multi-Mode Programmable Digital Cardiac Pacemaker"; U.S. Pat. No. 4,253,466 entitled "Temporary and Permanent Programmable Digital Cardiac Pacemaker"; and U.S. Pat. No. 4,401,120 entitled "Digital Cardiac Pacemaker with Program Acceptance Indicator".

Aspects of the programmer that is the subject of the foregoing Hartlaub et al. patents (hereinafter "the Hartlaub programmer") are also described in U.S. Pat. No. 4,208,008 to Smith, entitled "Pacing Generator Programming Apparatus Including Error Detection Means" and in U.S. Pat. No. 4,236,524 to Powell et al., entitled "Program Testing Apparatus". The Smith '008 and Powell et al. '524 patents are also incorporated by reference herein in their entirety.

A commercially available example of a programmer used for communicating with implanted medical devices is the Model 9790, manufactured by Medtronic, Inc., Minneapolis, Minn. The Model 9790 programmer is based on an general-purpose microprocessor platform, e.g., on an Intel 80x86 microprocessor or the like, and includes a text and graphics display screen similar to that conventionally used with personal computers. The graphics display screen allows graphical depictions, for example, of real-time cardiac electrical waveforms transmitted from the implanted device, to be presented to the physician or clinician. Additionally, for pacemakers which have a Marker Channel™ capability, the event markers associated with various physiologic and pacing events detected by the implanted device can be superimposed upon or displayed alongside an EGM or ECG waveform on the programmer's display, allowing the physician or clinician to observe the time relation between marker events and the EGM or ECG waveform. This gives the physician or clinician some degree of insight into whether the pacemaker is operating properly.

Heretofore, three basic techniques have been used for telemetric communication in an implantable device system: magnetic field coupling, reflected impedance coupling, and radio-frequency (RF) coupling. In static magnetic field coupling, of which the above-described Bowers '111 patent is an example, a static magnetic field is generated external to the medical device, e.g., using a permanent magnet, having sufficient strength to close a magnetic reed switch within the implanted device. While such a technique provides a fairly reliable mechanism for turning various functions within the implanted device on or off, the technique is, as noted above, much too slow for efficiently transferring any significant amount of data. Furthermore, for all practical purposes, the static magnetic system is useful only for downlink communication, not for uplink communication. Despite the limitations of magnetic coupling downlink communication, its simplicity and reliability are such that such arrangements can be found even in current devices, for example, the Medtronic Itrel II implantable neural stimulator, as substantially described in U.S. Pat. No. 4,520,825 to Thompson et al.

Dynamic magnetic field programming, on the other hand, relies upon the generation of a series of strong magnetic impulses which periodically actuate a magnetic reed switch inside the implanted device. The output of the reed switch circuit forms the programming input to data registers in the implantable device, as shown, for example, in the above-referenced to Terry, Jr. et al. '796 patent. Such arrangements have several limitations, including the rate at which strong magnetic impulses can be generated (several hundred hertz or so), the physical size of the reed switch and magnet, the sensitivity to magnetic field orientation, and necessity of generating the impulses in very close proximity to the implanted device.

In a reflected impedance coupling system, information is transferred using the reflected impedance of an internal (implanted) L-R or L-C circuit RF energized by an inductively coupled, external, L-R or L-C circuit. Such a system is shown, for example, in U.S. Pat. No. 4,223,679 to Schulman et al. Advantageously, such a system uses little or no current to transmit information. Disadvantageously, however, the maximum data rate of reflected impedance coupling systems is relatively slow, and the distance or rate at which information may be transferred is limited.

In RF coupled systems, which are perhaps the most commonly employed communication systems in modem implantable device systems, information is transferred from a transmitting coil to a receiving coil by way of a radio-frequency carrier signal. The carrier signal is modulated with the data that is to be transmitted using an appropriate modulation scheme, such as phase shift keying (PSK), frequency shift keying (FSK), or pulse position modulation (PPM), among numerous others. The modulated carrier induces a voltage in the receiving coil that tracks the modulated carrier signal. This received signal is then demodulated in order to recover the transmitted data. Because the stainless steel or titanium canister commonly used to hermetically enclose an implanted device acts as a low-pass filter for the transmitted RF signals, attenuation increases as frequency is increased. Devices currently on the market have a maximum frequency of less than 200-kHz. Also, the transmitting range has been limited to 2- to 3-inches or so.

An example of an RF communication system is shown in the above-referenced Thompson et al. '063 patent.

Depending upon the type of modulation and demodulation used in an RF communication system, the data or bit rate cannot exceed a predetermined fraction of the carrier frequency; otherwise, the ability to reliably distinguish between modulation representing a digital (binary) "1" from a digital "0" is compromised. Schemes are known which encode digital data to transmit more data per unit time and reduce implanted device current drain, as is shown in the above-reference Wyborny et al. '404 patent. However, at very high data transmission rates, the current drain would be very high.

RF communication programming units such as the above-noted Model 9790 programmer typically interface with the implanted device through the use of a programming head or programming paddle, a handheld unit adapted to be placed on the patient's body over the implant site of the patient's implanted device. In some cases, a magnet in the programming head effects reed switch closure in the implanted device to initiate a communication session (this is a safeguard against accidental programming of the device; otherwise, reed switch closure has little meaning as far as communication of information). Thereafter, uplink and downlink communication takes place between the implanted device's transmitter and receiver and a receiver and transmitter disposed within the programming head.

For most RF programming arrangements, both uplink and downlink signal strength vary as a function of programming head positioning. Thus, it is critical in many prior art systems for the programming head to be properly positioned over the patient's implant site, not only so that the magnet in the programming head is close enough to the implanted device to cause reed switch closure, but also so that the downlink RF signals can be detected in the implanted device and the uplink signals can be detected by the programming head. If the programming head is too far away from the implanted device, the attenuation of RF signals transmitted may be too great, preventing the communication link from being established.

Although both uplink and downlink signal strength vary as a function of head position, the coupling maps for uplink and downlink communication may be different. That is, what may be optimal positioning for uplink communication may be less optimal for downlink communication, and vice versa.

Differences between the uplink and downlink communication coupling maps commonly arise because of differences in the uplink and downlink transmission power and in the uplink and downlink receiver sensitivities Differences also occur when a so-called "dual-coil" system is employed in the programmer. An example of a dual-coil communication system is described in U.S. Pat. No. 4,542,532 to McQuilkin, entitled "Dual Antenna Receiver". The McQuilkin '532 patent is hereby incorporated by reference herein in its entirety. In a dual-coil system, two coils are connected in series opposition to achieve noise cancellation in the receive mode. The two coil series-opposing configuration makes the programmer sensitive to the curl of magnetic fields. Such curl sensitivity results in a significant increase in noise rejection over a single-coil antenna for in-band, spatially-aligned interference fields present in the proximity of the antenna.

For transmission from a dual-coil antenna, the two coils are configured in "parallel aiding" fashion, such that the magnetic field transmitted by the antenna is effectively doubled.

Often, medical device programmers, for example the Model 9790 programmer referred to above, are provided with a Head Positioning Indicator, either audible or visible, for indicating to the physician or clinician when the programming head is properly located over a patient's implanted device. In the prior art, the technique most commonly used for determining when the programming head is properly positioned can be characterized generally as "open loop", in that the determination of correct head positioning is based solely upon an assessment of whether the uplink signal (i.e., the signal transmitted from the implanted device to the external programming head) meets some minimum requirement. In particular, uplink signal strength is measured based upon the operating gain of the uplink communication receiver. In such open loop verification systems, adequate downlink signal strength is not tested.

An example of an open loop system for determining the proper positioning of a programming head is described in U.S. Pat. No. 4,531,523 to Anderson, entitled "Digital Gain Control for the Reception of Telemetry Signals From Implanted Medical Devices". The '523 patent relates to a system wherein verification of the programming of an implanted device is provided by the transmission of predetermined signals from the implanted device. When errors are detected in these uplink signals, the number of errors are counted over a period of time. If more than a predetermined number of errors occur in that time, the gain of the programming unit receiver is adjusted downward by a predetermined amount. This adjustment continues until uplink signals are received without error. As an open loop system, however, the system of the '523 patent does not test for errors in downlink signals, and does not evaluate the strength of the received downlink signals.

When downlink signal strength cannot be tested, it is important for the physician or clinician to be able to otherwise verify that programming signals transmitted from the programming head are accurately received and processed by the implanted device. To this end, a system is described in the above-referenced Hartlaub et al. '120 patent wherein circuitry in the implanted device performs several different checks on the detected downlink programming signal, including a parity check and an access code check, and issues a program acceptance signal if the downlink programming is found to be valid.

As those of ordinary skill in the art will appreciate, a communications protocol using common handshaking can verify that a minimum downlink field strength for detection in the implanted device exists prior to signaling the physician or clinician that correct head positioning has been achieved. However, a handshaking protocol cannot provide any information useful for optimization of head positioning to ensure an adequate operating margin. This means that proper programming head positioning may be indicated even though the programming head is actually marginally positioned, such that a very slight shift in positioning (e.g., due to patient motion) results in downlink communication failure.

Those of ordinary skill in the art will appreciate that one possible way to ensure an adequate margin between the strength of detected downlink signals in an implanted medical device and the device's detection threshold would be to transmit downlink signals having much larger than nominal amplitudes. From an energy consumption standpoint, this solution is particularly feasible when used in the context of a line-powered (as opposed to battery-powered) external programming unit, since for a line-powered programming unit, energy consumption is not a critical factor. If extremely strong downlink signals were transmitted, the programmer could be assured that the signals will be strong enough to be detected by the implanted device. In this way, the need for a downlink signal strength indication would be obviated.

There are several disadvantages beyond radio regulatory compliance, however, associated with the use of excessively strong downlink signals to ensure their detection by the implanted device. First, while power consumption is not a crucial factor in line-powered programmers, it is becoming increasingly common for programming units to be portable and battery-powered, so that they may be easily transported and used in a variety of clinical and/or non-clinical settings. For battery-powered programmers, it would be inefficient and undesirable to consume the limited battery power with unnecessarily high-level downlink signals.

Perhaps a more critical disadvantage of transmitting high-level downlink signals is the possibility that the large RF energy bursts in the downlink transmission may interfere with the operation of the implanted device. In particular, for very high-energy downlink pulses, it is possible for the downlink signal to induce voltages on implanted pace/sense leads. Such induced voltages may be interpreted by the implanted device's sensitive sensing circuitry (e.g., pacemaker) as cardiac events and may thereby cause pacemaker inhibition or lead to loss of synchronization with intrinsic cardiac activity. This problem is likely to worsen as improved (i.e., more sensitive) sensing circuitry is developed.

In the prior art, implanted devices have been provided with clamping diodes to prevent overdriving of the implanted devices' communication system inputs and circuitry to dissipate energy induced in the implanted downlink receiver coil. For example, energy induced in a device's receiver coil can to a limited extent be redirected to the device's battery.

Nonetheless, problems with excessive energy from downlink signals are likely to be exacerbated in state-of-the-art and future devices to which more and more information must be communicated over relatively long periods of time.

A further problem arising from the inability in prior art programing arrangements to ascertain the strength of the downlink signal as detected by the implanted device is that communication failures are difficult to troubleshoot. This is due, in part, to the fact that when downlink signals are not successfully received, the programmer cannot tell whether the problem lies in the positioning of the programming head, in inadequate downlink signal strength, or elsewhere.

The use of a secondary (feedback) sensing coil within the programmer itself to sample the downlink signal intensity within the programming head compensates for such variables as supply voltage variation, temperature-induced variation, parts tolerance variation, transmit antenna detuning and transmit antenna loading. However, a sensing coil does not compensate for field distortions beyond the programming head that do not result in intensity changes in the feedback sensing coil. The field is merely standardized and does not dynamically adjust to compensate for field distortion or attenuation that occurs in and around the implanted device itself, nor for the alignment of the electromagnetic field vector with the implanted device's downlink sensing vector.

As a result of the foregoing considerations, it has been recognized as desirable to provide a programmer with the capability of evaluating the strength of downlink signals as detected by the implanted device, i.e., to enable the implanted device to communicate to the programmer information about the strength of downlink signals received by the implanted device. Such capability is particularly desirable in the context of dual-coil systems, wherein the uplink and downlink coupling maps are different due to the different coil configurations used in the programmer for transmission and reception. With such a capability, the programmer can dynamically adjust the amplitude of downlink pulses, such that downlink signals would be transmitted at a level known to exceed the implanted device's detection threshold. At the same time, the programmer can minimize transmission of excessively or unnecessarily large downlink signals which could lead to the aforementioned problems with receiver overdriving, pacemaker inhibition due to induced voltages applied to the sensing circuitry, and the like.

A communication arrangement in which both uplink and downlink signal strength can be independently assessed can be described as a "closed loop," in that the assessment of downlink signal strength is not inferentially made based upon uplink signal strength. Thus, in closed-loop communication arrangements, the differences between the uplink and downlink coupling maps is accounted for. One example of this is described in U.S. Pat. No. 5,324,315 to Grevious, entitled "Closed Loop Downlink Telemetry and Method for Implantable Medical Device." According to the '315 patent, the implanted device is provided with the capability of evaluating the strength of the downlink signal and is able to communicate to the external programming unit information about the strength of downlink signals after they have been received by the implanted device. Such a system allows programmer downlink adjustment to adequately exceed the implantable device's receive threshold without using excessively large downlink signals and causing the aforementioned device function anomalies. Likewise, uplink signal strength assessment enables the programmer to cause an implanted device to increase its uplink signal strength, if inadequate uplink reception is detected, or to decrease its uplink signal strength if more than adequate uplink reception is detected. In the latter case, the implanted device's battery longevity is maximized, through minimization or elimination of unnecessary current drain on the battery.

A further advantage of closed-loop downlink signal strength assessment is that if the received downlink can be controlled, programmers with very high output level capabilities could be used to extend the range of the system.

SUMMARY OF THE INVENTION

Implementation and operation of most, if not all, RF communication systems involves a balancing or compromising of certain countervailing considerations, relating to such interrelated operational parameters as data transmission rate and transmission range, among numerous others. Such operational parameters are often interrelated in the sense that the adjustment of one operating parameter may permit or require the adjustment of one or more other operating parameters even while predetermined system performance goals and/or requirements continue to be met and predetermined limitations imposed upon operational parameter adjustment are adhered to. One example of this is the trade-off between signal range and signal power. Simply stated, for a given communication scheme, a more powerful (e.g., higher amplitude) signal has a longer effective range. Thus, decreasing the range of a communication link (e.g., reducing the distance between transmitters and receivers in the link) allows the transmission power to be decreased, while other operational parameters, e.g., data transmission rate, can be held at a constant value.

Another example is the trade-off between data transmission rate and transmitted signal power. Those of ordinary skill in the art will appreciate that in most instances, increasing the data transmission rate over an RF channel typically requires increased signal bandwidth. Increasing the bandwidth, in turn, tends to lead to increased power consumption by the communication system in order to maintain an acceptable signal-to-noise ratio.

Still another example of the trade-offs associated with the operational parameters, and system performance goals of an RF communication system is that associated with data transmission rate versus signal range. As noted above, increasing data transmission rate typically requires increasing the bandwidth of the transmitted signals; conversely, decreasing data transmission rate typically allows for a reduction in the signal bandwidth. If bandwidth can be reduced, the range of operation will be increased for a given level of power consumption.

As noted above, the foregoing and other trade-offs associated with various operational parameters of a communication system arise in most applications involving RF transmission and reception, although the nature of the interrelation between the various operational parameters may vary depending, for example, upon the type of modulation used (pulse position modulation, frequency shift keying, frequency modulation, amplitude modulation, etc. . . ), as well as upon the type of coding used. In the context of implantable medical device systems, there are additional considerations that must be addressed. Primary among these are reliability of transmission and reception, and conservation of implanted device power. Conservation of implanted device power (which in most cases implies minimization of current drain upon an implanted device's internal battery) in particular renders the aforementioned trade-offs—rate-versus-range, range-versus-power, rate-versus-power, etc. . . —highly significant. In most cases, however, the settings of operational parameters of interest are static, or if adjustable, are adjusted simply using a single parameter such as signal amplitude.

In view of the foregoing considerations, the present invention is directed to a method and apparatus for establishing and maintaining an optimized communication link between two or more electronic devices, such as between implanted medical devices and external programming/ control units, or between two or more implanted devices.

In one embodiment of the invention, an implantable device is provided with a communication system which includes circuitry for monitoring various operational parameters and operating conditions and constraints of the communication link. The communication system further includes control circuitry and operational parameter adjustment circuitry for dynamically adjusting multiple interrelated operational parameters of the communication link, such that system performance goals are met and system optimization is continuously achieved. System performance goals may be defined differently depending on the particular circumstances of device operation. Multiple, prioritized performance goals may be specified for each of a number of different operational circumstances, with operational parameters correspondingly automatically to meet as many of the performance goals, in order of priority, as circumstances allow.

For example, the invention may be embodied in an implantable pacemaker, defibrillator or other device and an associated programmer or controller which are intended to be used to transmit different types of information which require differing degrees of accuracy and differing rates of data transmission, such as device control information, real time telemetry of measured physiologic parameters or telemetry of stored information. Similarly, the programmer and implantable devices may be intended for use in differing situations, for example, situations in which the transmitting and receiving antennas of the implantable device and the programmer are either closely adjacent to one another or spaced apart by a substantial distance. In the context of an implantable device communicating with an external programmer, or communicating with a second implantable device, the performance goals may also differ depending on the direction of the transmissions. The present invention, by having the flexibility to adjust a number of operational parameters can select the specific parameters for adjustment which optimize the transmission link to accomplish the performance goals defined by the operational circumstances and types of data being transmitted.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein:

FIG. 6 is a block diagram of the transmitter from the implanted device communication system of FIG. 5; and FIG. 7 is a block diagram of the receiver from the implanted device communication system of FIG. 5.

DETAILED DESCRIPTION OF A SPECIFIC EMBODIMENT OF THE INVENTION

Figure 1:
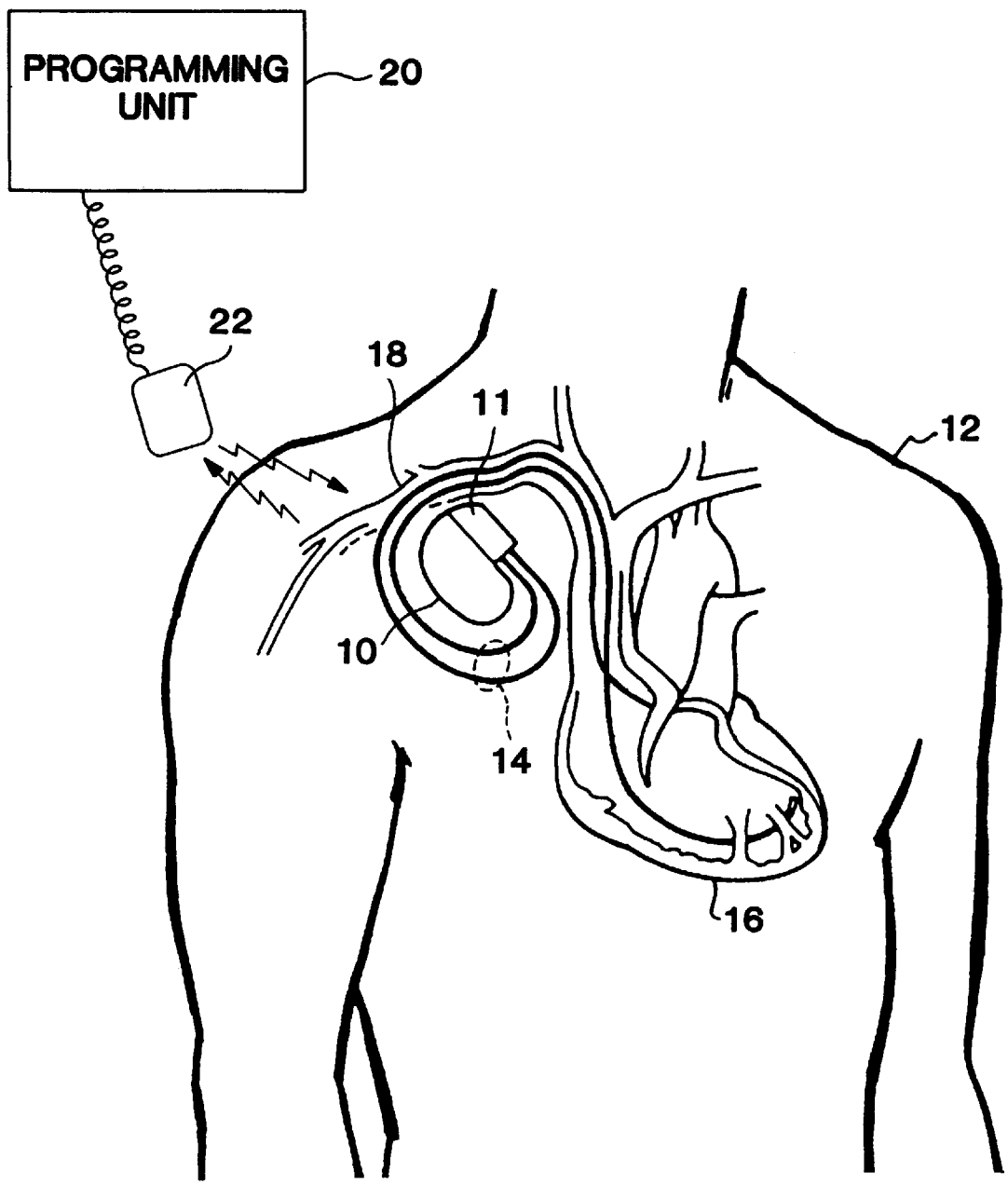
FIG. 1 is an illustration of a body-implantable device system in accordance with one embodiment of the invention, including a hermetically-sealed device implanted in a patient and an external programming unit.

Referring to FIG. 1, there is shown an illustration of an implantable medical device system adapted for use in accordance with one embodiment of the invention. The medical device system shown in FIG. 1 includes an implantable device 10—a pacemaker in this embodiment—which has been implanted in a patient 12. In accordance with conventional practice in the art, pacemaker 10 is housed within a hermetically sealed, biologically inert outer canister, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extends into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in either the atrium or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennas within the head can send RF signals to, and receive RF signals from, an antenna disposed within the hermetic enclosure of the implanted device or disposed within the connector block of the device, in accordance with common practice in the art.

Figure 2:
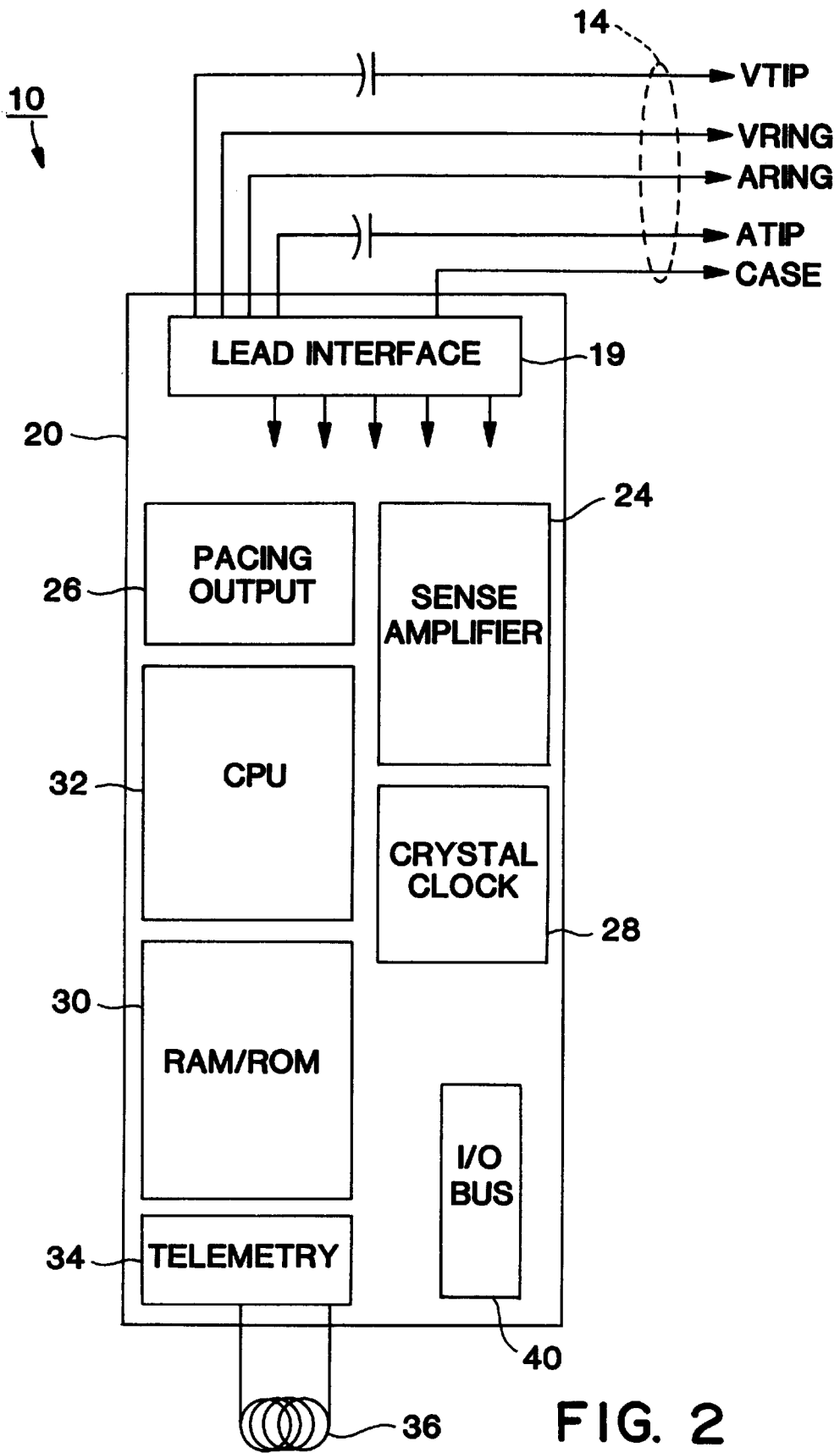
FIG. 2 is a block diagram of the implanted device from FIG. 1.

Turning now to FIG. 2, there is shown a block diagram of the electronic circuitry which makes up pulse generator 10 in accordance with the presently disclosed embodiment of the invention. As can be seen from FIG. 2, pacemaker 10 comprises a primary stimulation control circuit 20 for controlling the device's pacing and sensing functions. The circuitry associated with stimulation control circuit 20 may be of conventional design, in accordance, for example, with what is disclosed the above-referenced to Sivula et al. '388 patent. To the extent that certain components of pulse generator 10 are conventional in their design and operation, such components will not be described herein in detail, as it is believed that design and implementation of such components would be a matter of routine to those of ordinary skill in the art. For example, stimulation control circuit 20 in FIG. 2 includes sense amplifier circuitry 24, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable communicating with external programmer/control unit 20, as will be hereinafter described in greater detail.

With continued reference to FIG. 2, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1 but not shown in FIG. 2. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 2, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, stimulation control circuit 20 includes central processing unit 32 which may be an off-the-shelf programmable microprocessor or microcontroller, but in the presently preferred embodiment of the invention is a custom integrated circuit. Although specific connections between CPU 32 and other components of stimulation control circuit 20 are not shown in FIG. 2, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 2, crystal oscillator circuit 28, in the presently preferred embodiment a 32,768-Hz crystal controlled oscillator, provides main timing clock signals to stimulation control circuit 20. Again, the lines over which such clocking signals are provided to the various timed components of pulse generator 10 (e.g., microprocessor 32) are omitted from FIG. 2 for the sake of clarity.

It is to be understood that the various components of pulse generator 10 depicted in FIG. 2 are powered by means of a battery (not shown) which is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits which would be suitable for the purposes of practicing the present invention.

Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). These event-indicating signals are provided to CPU 32 for use by CPU in controlling the synchronous stimulating operations of pulse generator 10 in accordance with common practice in the art. In addition, these event indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 34 in pacemaker 10, and an associated communication subsystem in external unit 20.

Figure 3A:
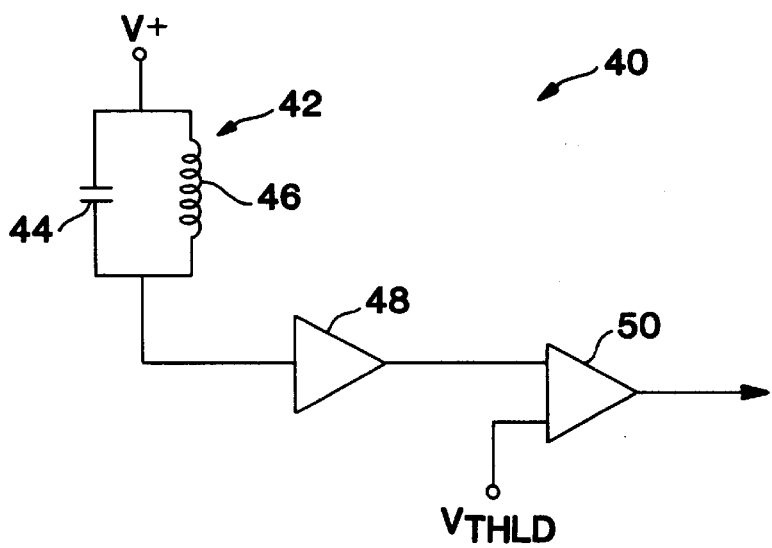
FIG. 3a is a block diagram of a prior art receiver.

In FIG. 3a, there is shown a simplified schematic representation of a prior art RF communication receiver 40 such as is typically found in implantable medical device systems. Receiver 40 utilizes an antenna, designated generally as 42 in FIG. 3a, which in accordance with common practice in the art comprises a capacitor 44 in parallel with an inductive coil 46. The output of antenna 42 is applied to the input of an amplifier 48 which amplifies RF signals received by antenna 42. The output from amplifier 48 is applied to one input of a comparator circuit 50, which receives at its other input a threshold voltage $V_{THLD}$. A received data output pulse is generated from comparator 50 whenever the amplified received signal exceeds the level of $V_{THLD}$. The information content of the received signal may then be extracted from the stream of output pulses from comparator 50 through appropriate demodulation.

Figure 3B:
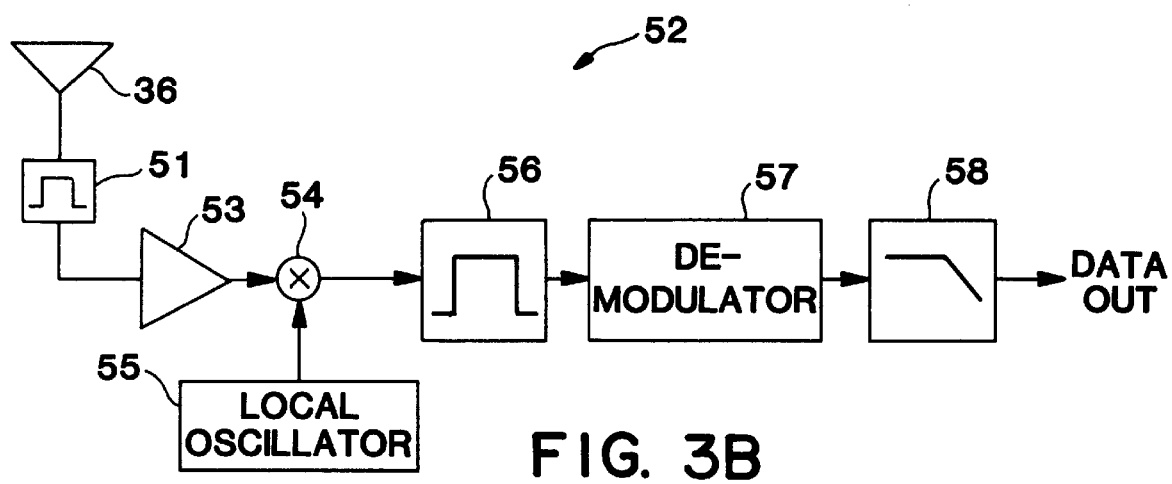
FIG. 3b is a block diagram of a heterodyne frequency shift keyed receiver in accordance with one embodiment of the invention.

Turning now to FIG. 3b, there is shown a schematic representation of a heterodyne frequency shift keyed communication receiver 52 in accordance with one embodiment of the present invention. It is believed that the following brief description of the operation of receiver 52 will provide some useful background information and terminology to form the basis of an understanding of the present invention.

Receiver 52 is coupled to antenna 36, which can take the form of a conductive coil in which a current is induced by transmitted RF signals or, alternatively, a pacing lead wire used as a radiating monopole antenna element. For signal reception by antenna 36, the induced signal in antenna 36 is first bandpass-filtered in preselector bandpass filter 51 and amplified by an amplifier 53, the output of which being then applied to one input of a mixer (multiplier) 54. Mixer 54 also receives a local oscillator input signal from local oscillator 55. As will be appreciated by those of ordinary skill in the art, mixer 54, with an appropriate local oscillator frequency, down-converts the signal received on antenna 36, through low-side injection and/or high-side injection to an intermediate frequency (IF). (The IF may be 0-Hz in a direct conversion system.) The mixed signal from mixer 54 is then applied to a bandpass filter 56 having a passband centered at the system's intermediate frequency. The bandpass filtered signal is then applied to demodulator block 57, the nature of which varying depending upon the type of modulation (e.g., frequency modulation, pulse position modulation, etc . . . ) performed on the transmitted signal. The demodulated signal is applied to a baseband filter 58 to yield the extracted information content of the received signal.

For a receiver such as receiver 52 of FIG. 3b, the "receiver noise floor" (RNF)—the amount of noise introduced into the received signal in an otherwise noiseless environment—is given by the following expression:

$$RNF = K \times T \times B \times ReceiverNoiseFloor$$

where K is Boltzman's constant, T is temperature in degrees Kelvin, and B is the system bandwidth (in Hz), which is determined by the width of the passband of bandpass filter 56. Thus, for a hypothetical 200-kHz bandwidth and a receiver noise factor (Rx noise factor) of 1, the RNF is given by:

$$\begin{aligned} RNF &= K \times T \times B \times Rx\text{NoiseFactor} \\ &= \left(1.38 \times 10^{-23} \frac{\text{joules}}{\text{Kelvin}}\right) \times (300 - K) \times (200 \text{ kHz}) \times (1) \\ &= 8.28 \times 10^{-16} \frac{\text{joules}}{\text{sec}} = -150.8 \text{ dB}m \end{aligned}$$

For a given signal-to-noise ratio (SNR), expressed in decibels of relative power of signal amplitude divided by RNF in the bandwidth of interest, a certain bit error rate (BER) will result. That is, due to noise in the receiver, an occasional bit in the received signal will be incorrectly demodulated. As an example, for non-coherent synchronous frequency shift keyed (FSK) demodulation, an SNR of 13.4 dB produces a BER of 1E-5, i.e., one bit out of one hundred will be erroneously demodulated.

Since SNR and BER are related, for a given BER the necessary power of the received signal, PREC, can be computed as the sum of RNF plus SNR. Thus, continuing with the above example, if a maximum BER of 1E-5 is required in a given application (one example of the aforementioned system performance goals which may be defined for an implantable device system), the necessary power $P_{REC}$ of the received signal (i.e., the signal at the antenna) is −120.8 dBm+13.4 dB=−107.4 dBm. Of course, the power of the signal at the antenna is a function of the transmission range; also, all of the above computations assume an otherwise noiseless environment. The relationship between BER and SNR also holds for systems that are not thermally noise limited.

The foregoing discussion provides an illustration of some of the aforementioned trade-offs or compromises associated with the operational parameters of an RF communication system. For example, the above computations show that since the RNF of receiver 52 is a function of the system bandwidth, reducing the system bandwidth can lead to a reduction in the RNF. However, reducing system bandwidth necessitates a corresponding reduction in data transmission rate. This assumes that, as a system performance goal, a constant BER is to be maintained; alternatively, modification of the BER for a given transmission can improve the range (for example, during EGM transmission which does not require as great a data rate). On the other hand, increasing the transmission rate requires a corresponding increase in system bandwidth, introducing more noise into the system (i.e., increasing the RNF) for a given SNR, thereby necessitating an increase in power to meet the system performance goal of maintaining a given BER at a given range or path loss. Similar changes in system performance can be obtained by changing the coding scheme.

In view of the interrelation of various parameters of an RF system, such as bandwidth, BER, SNR, and RNF, the present invention contemplates a system in which the balancing and/or optimization of certain system conditions and operational parameters on a dynamic basis, such that the system is optimized in terms of performance and power consumption on an ongoing basis, and such that system performance goals are met, as will be hereinafter described in further detail.

Figure 4:
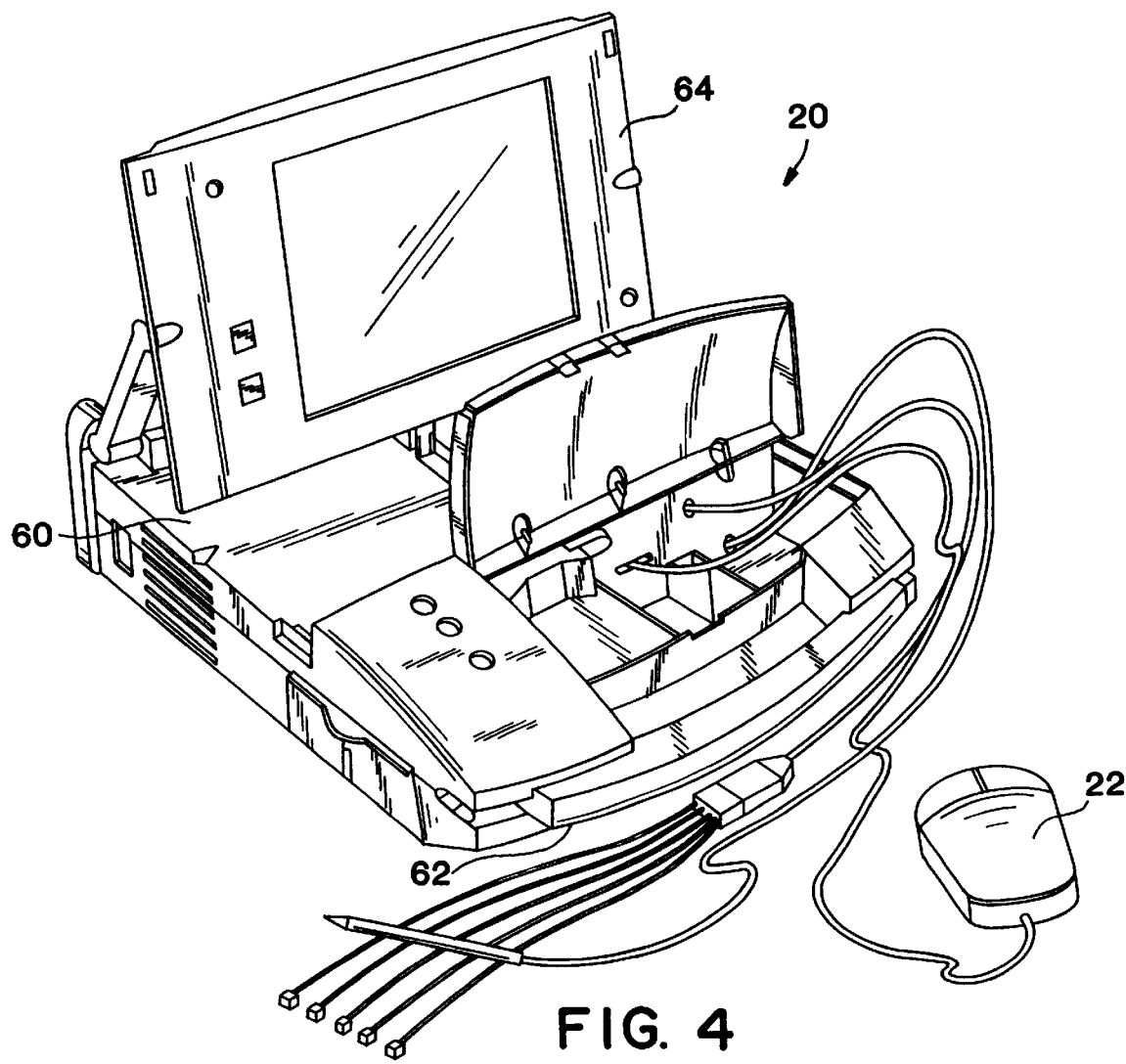
FIG. 4 is a perspective view of the external programming unit of FIG. 1.

In FIG. 4, there is shown a perspective view of programming unit 20 in accordance with the presently disclosed embodiment of the invention. Internally, programmer 20 includes a processing unit (not shown in the Figures) which in accordance with the presently disclosed embodiment of the invention is a personal computer type motherboard, e.g., a computer motherboard including an Intel 80x86 microprocessor and related circuitry such as digital memory. The details of design and operation of the programmer's computer system will not be set forth in detail in the present disclosure, as it is believed that such details are well-known to those of ordinary skill in the art.

Referring to FIG. 4, programmer 20 comprises an outer housing 60, which is preferably made of thermal plastic or another suitably rugged yet relatively light-weight material. A carrying handle, designated generally as 62 in FIG. 4, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 54 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for programmer 20 to adapt its mode of operation depending upon the type of implanted device to be programmed. Accordingly, it may be desirable to have an expansion cartridge containing EPROMs or the like for storing program information to control programmer 20 to operate in a particular manner corresponding to a given type of implantable device.

In accordance with the presently preferred embodiment of the invention, programmer 20 is equipped with an internal printer (not shown) so that a hard-copy of a patient's ECG or of graphics displayed on the programmer's display screen 64 can be generated. Several types of printers, such as the AR-100 printer available from General Scanning Co., are known and commercially available.

In the perspective view of FIG. 4, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 4 is described in more detail in copending U.S. Pat. No. 5,345,362 issued to Thomas J. Winkler, entitled "Portable Computer Apparatus With Articulating Display Panel," which patent is hereby incorporated herein by reference in its entirety. Also, the Medtronic Model 9760 or 9790 programmers are other implantable device programming units with which the present invention may be advantageously practiced.

Figure 5:
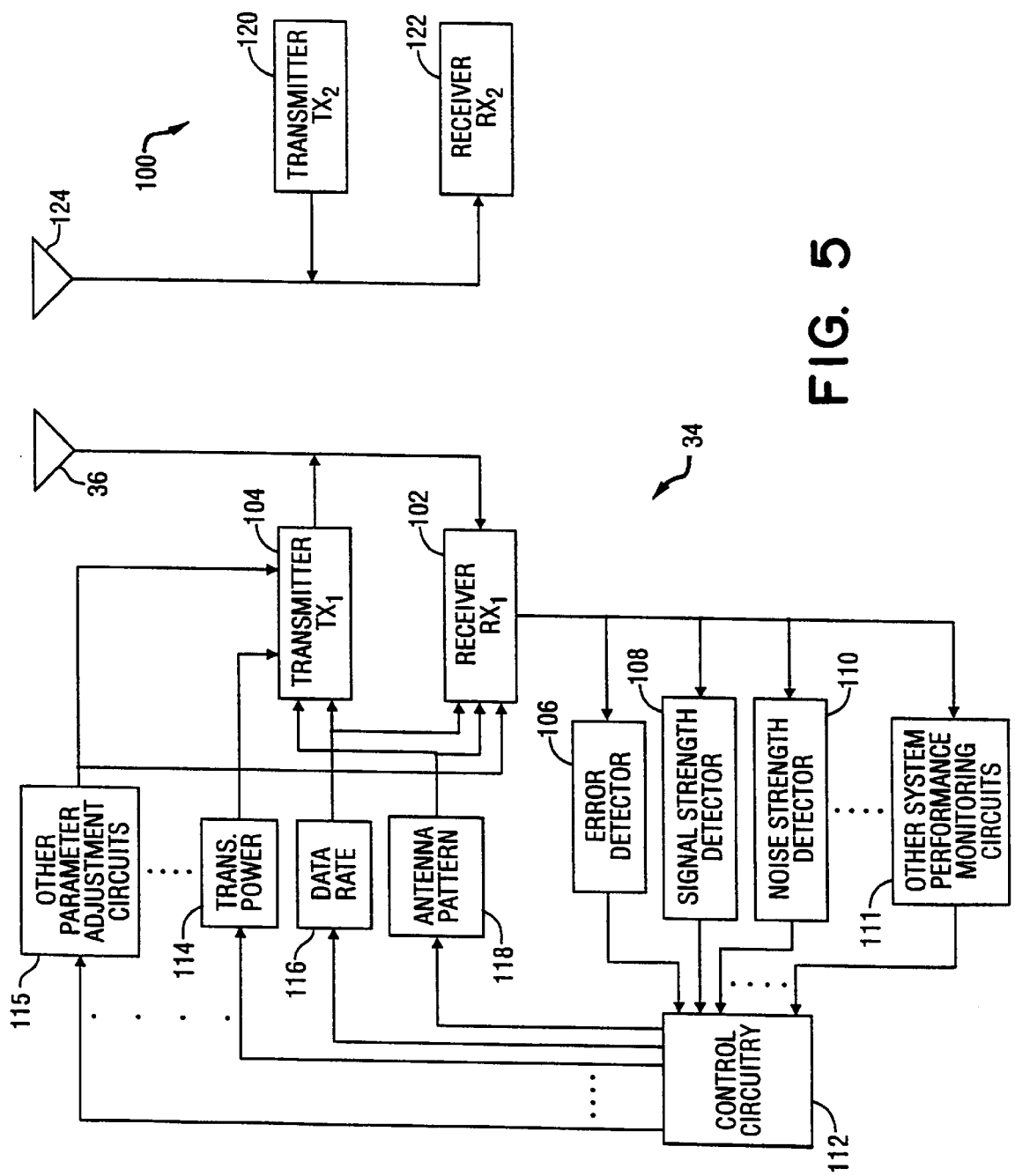
FIG. 5 is a block diagram showing the communication system in accordance with the present invention from the implanted device of FIG. 2 and a similar communication system from the external programming unit from FIG. 4.

Turning now to FIG. 5, there is shown a simplified block diagram of communication subsystem 34 from pacemaker 10, in accordance with one embodiment of the present invention. Also part of FIG. 5 is an even more simplified block diagram of a communication subsystem 100 associated with external programming unit 20. Communication subsystem 100 is preferably identical to communication subsystem 34 in implanted device 10. For simplicity in the Figures, however, only a transmitter 120, receiver 122 and antenna 124 from communication subsystem 100 are represented in FIG. 5.

Communication subsystem 34 in implantable device 10 includes a receiver 102 and a transmitter 104 each coupled to antenna 36 which, as previously noted, may be implemented as a multiple-turn wire coil, a stub wire, or a pacing lead. Communication subsystem 34 further includes, in one embodiment, error detection circuitry 106, signal strength detection circuitry 108, and noise strength detection circuitry 110. Generally speaking, error detection circuit 106, signal strength detection circuit 108, and noise strength detection circuit 110, can be called system performance monitoring circuits which function, as that name suggests, to dynamically monitor one or more aspects of communication system 34. Error detection circuit 106, for example, may utilize wellknown error detection techniques to determine the bit error rate (BER) and the SNR of digital information received by receiver 102. Signal strength detector circuit 108 may effectively consist of a logarithmic amplifier which detects and filters the RF signal (or IF signal if downconverted) to provide an RSSI (received signal strength indicator) output that gives a voltage proportional to the logarithm of the signal strength at the receiver's RF input. Detector 108 will only respond to the signal present within the receiver passband. In this way, the desired signal strength (actually, signal plus noise) can be measured. Likewise, the noise can be measured with the same apparatus under the condition of a known period with no received transmission. In this way the signal-to-noise ration of the received signal can be measured by a simple comparison of the signal and the noise RSSI samples. This method, as would be appreciated by those of ordinary skill in the art, would effectively implement circuit 110 as well as 108 in FIG. 5.

With continued reference to FIG. 5, circuits 106, 108 and 110 are in turn coupled to a control circuit 112 which, in one embodiment, may be a custom integrated circuit or the like or, when part of subsystem 100, may be part of the PC-type computer platform of programmer 20 described above. Control circuit 112 in communication subsystem 34 functions to control various aspects of communication operation in device 10, and further functions to cause commands to be transmitted to communication subsystem 100 to cause adjustment of operational parameters therein. For example, as shown in FIG. 5, control circuit 112 is coupled to a transmitter power control circuit 114, such that under command of control circuit 112, the power of signals transmitted by transmitter 104 can be adjusted up or down. Similarly, control circuit 112 is coupled to a data rate control circuit 116 which controls the rate at which data is transmitted from transmitter 104. Control circuit 112 is also coupled to an antenna pattern (field strength as a function of position) control circuit 118, so that the antenna pattern for reception and transmission of transmitted signals may be dynamically configured during operation of communication subsystem 34 and to receiver circuit 102 so that the bandwidth of the bandpass filter therein may be adjusted.

Control circuit 112 is responsive to prioritized sets of operational goals to be accomplished in conjunction with each of a plurality of telemetry transmission types, stored in RAM/ROM 30 (FIG. 2). In response to an identification of the type of telemetry to follow, processor 32 (FIG. 2) instructs control circuit 112 as to operational parameters and through control circuitry 112 monitors the outputs of the performance monitoring circuits 106, 108, 110, 111. Under control of processor 32, control circuitry adjusts the various parameter adjustment circuits to achieve the operational goals stored in RAM/ROM 30, in order of their priorities. Control circuitry 112 in some cases adjusts the operational parameters associated with transmitter 104 or receiver 102. Alternatively, parameter adjustment commands may be formatted by processor 32 for transmission by transmitter 104 to receiver 122, to control corresponding parameter adjustment circuits associated with transmitter 120. Specific examples of the operation of the parameter adjustment circuits and the performance monitoring circuits are set forth in more detail below.

As noted above, the description of error detection circuit 106, signal strength detection circuit 108, and noise strength detection circuit 110 in communication system 34 of FIG. 5 is intended merely to be illustrative of the types of operational parameters which may be involved in the dynamic optimization system in accordance with the present invention, and it is contemplated that various other types of operational parameter monitoring circuits may be included in a communication system in accordance with the present invention. This possibility is reflected by the inclusion in FIG. 5 of other system performance monitoring circuits block 111 and other parameter adjustment circuits block 115. For example, an additional aspect of system performance that may be advantageously monitored in accordance with the present invention is the local electromagnetic environment, i.e., the presence of, level of, and frequency of radio-frequency signals from sources other than the telemetry system itself (i.e., RF "noise"). Such signals could interfere with telemetry transmission. If a noise monitoring circuit were included among other system performance monitoring circuits 111, it would then be possible to include a frequency selecting circuit among parameter adjustment circuits 115 in FIG. 5, for causing transmitter 104 to dynamically adjust its transmitter frequency to a transmitter frequency at which the least amount of noise is detected by the noise monitoring circuit 115. It is believed that the design and implementation of a suitable noise detection circuit (e.g., a simple spectrum analyzing circuit for detecting RF signals in the range of frequencies of interest, for example, 174- to 216-MHz) would be a matter of routine engineering to a person of ordinary skill in the art. Similarly, it is believed that it would be a matter of routine to implement transmitter 104 such that is capable of transmitting at one of a plurality of frequencies. Before adjusting its frequency, transmitter 104 can send a notification message to receiver 122 alerting receiver 122 that subsequent transmissions will occur at a different frequency. It is believed that such capability would enable telemetry system 34 to be less susceptible to interference from noise and other local RF signals.

Similarly, included among performance monitoring circuits 111 and parameter adjustment circuits 115 may be circuitry for monitoring error rates, noise, etc . . . in the telemetry signal and for causing transmitter 104 to alter its modulation type and/or encoding type. The types of operational parameters which may be monitored and adjusted in accordance with the principles of the present invention may vary, depending, for example, upon the parameters deemed to be of critical concern in a given application and the nature of the transmitters and receivers used to establish a communication link.

In accordance with an important aspect of the invention, communication subsystems 34 and 100 are preferably capable of exchanging information with each other, such that each one can cause adjustment of certain operational parameters of the other. For example, if signal strength detector circuit 108 in subsystem 34 determines that the received signal transmitted from transmitter 120 is unacceptably weak, control circuitry 112 can initiate transmission of a command to subsystem 100 instructing transmitter 120 to increase its transmission power.

Circuits 114, 116, and 118 may generally be referred to as operational parameter adjustment circuits, in that they are each coupled to some component of communication circuit 34 in order to control some aspect of the operation of communication circuit 34. As noted above, for example, under command of control circuit 112, data rate circuit 116 can adjust the data transmission rate of transmitter 104 up or down. Additional operational parameters which may be adjusted include the power level of the transmission, the number of repetitions of the transmitted data and the frequency chosen for transmission of the data.

Error detection circuit 106, signal strength detection circuit 108, and noise strength detection circuit 110 are merely examples of system performance monitoring circuits which may be included in communication system 34. It is contemplated that one or more additional system performance monitors, represented collectively by block 111 in FIG. 5, may be included in communication system 34 depending upon the circumstances surrounding implementation thereof, as will be hereinafter described in further detail. Likewise, communication system 34 may include additional operational parameter adjustment circuits, as represented by block 115 in FIG. 5.

An important principle underlying the present invention involves the dynamic monitoring, allocation, and adjustment of interrelated operational parameters associated with the communication system, such that some marginal level of overachievement with regard to one operational parameter may be reapplied to the benefit of another operational parameter, leading to an overall increase in system performance. That is, if one operational parameter is adjusted to a point where system performance in some aspects exceeds predetermined minimum standards, that operational parameter and/or others, on both ends of the communications link, may be readjusted so as to maintain system performance above such standards and at the same time realize improvements or optimization with regard to other aspects of system performance.

As an example of this concept, if error detection circuit 106 in communication system 34 of FIG. 5 determines (and so informs control circuitry 112) that the BER of the signal received by receiver 102 is lower than what is deemed to be the maximum required or acceptable BER for the system, control circuitry 112 can take advantage of this margin of system performance above minimum acceptable standards by either (1) instructing transmitter 120 to decrease its transmission power, thereby reducing current drain on the power supply of subsystem 100; (2) instructing transmitter 120 to increase its data rate, thereby potentially increasing the in the signal received by receiver 102, BER but also increasing system efficiency and the speed with which information can be communicated across the link; or (3) leaving transmission rate and transmission power unchanged but informing system 100 that the range of the link may be increased. In any case, the existence of a margin of some aspect of system performance above minimum standards (in this example, the better-than-necessary BER) is exploited, leading to enhancement or optimization of other aspects of system performance.

As another example, signal strength detector circuit 108 in communication system 34 of FIG. 5 may determine that the strength of the signal received by receiver 102 exceeds some predetermined minimum level. In that case, control circuit 112 can cause transmitter 104 to transmit an instruction to transmitter 100 in external unit 20 to either (1) decrease transmission power for transmitter 120, or (2) take advantage of the excessive signal strength by increasing the data transmission rate of transmitter 120. Alternatively, if neither of these actions is taken, the maximum allowable range for the link is increased.

Thus far, the present invention has been described in terms of detection of aspects of system performance which are found to exceed predetermined minimum standards. The present invention also has applicability in circumstances where some aspect of system performance is found to be unacceptably poor. For example, error detection circuit 106 may determine that the BER of the signal received by receiver 102 is higher than what is deemed acceptable for the link. In that case, control circuit 112 can cause transmitter 104 to transmit an instruction to external unit 100 to either (1) increase the transmission power of transmitter 120, or (2) decrease the data transmission rate of transmitter 120, or provide the operator with information regarding how to increase link performance (e.g., an audio or visual indicator).

This last consideration—the type of transmitters and receivers used to implement the link—is believed to have a particularly significant impact upon the types of operational parameter monitoring that should be performed in the practicing of the present invention. The types of monitoring described so far with reference to the system of FIG. 5 are believed to be more or less applicable generally to any type of communication system implementation. Other additional types of monitoring may be appropriate depending upon the specific nature of the communication system. For example, in a pulse position modulated communication link, in which binary ones and zeros are distinguished based upon the time interval between transmitted pulses, one operational parameter for which monitoring and dynamic adjustment would be appropriate is the inter-pulse width of the signal. Then, if it is desired to decrease the BER of the transmitted signal, one approach in this case would be to increase the pulse repetition rate (or, alternatively, to increase the number of pulses integrated per bit), at the expense of decreased data transmission rate.

For an uncoded heterodyne frequency shift keying system such as described herein in general terms with reference to FIG. 3b, one operational parameter which would be advantageously monitored and dynamically adjusted in accordance with the principles of the present invention is the signal-to-noise ratio (SNR), which may be obtained from the outputs of signal strength detection circuit 108 and noise strength detection circuit 110. If it is determined in such a system, for example, that a higher data transmission rate is desirable or necessary, the system as described above can respond by increasing the data transmission rate. Such an increase, however, necessitates a greater intermediate frequency bandwidth, which means that a decrease in the SNR will likely be detected. The decreased SNR may go to an unacceptable level, thus necessitating an increase in data transmission power. This example illustrates the aforementioned trade-off between the operational parameters of transmission rate and transmission power. Note that similar trade-offs in performance can be obtained in coding.

Similarly, in some applications it may be desirable or necessary to increase the range of the link. In that case, control circuitry 112 can cause transmitter 104 to transmit at a decreased transmission rate, so that a lower intermediate frequency bandwidth is required, for a given transmission power level. Theoretically, reducing transmission rate by a factor often will increase the received SNR by a factor often. Since range in a far-field system falls off as $1/R^2$ (where R is the range of the link), this means that for a given SNR, range is increased by the square root often times (approximately 3.162 times) as a result of the tenfold decrease in transmission rate. This illustrates the aforementioned trade-off between the operational parameters of transmission range and transmission rate, for a given SNR.

The aforementioned trade-off between the operational parameters of transmission range and transmission power is perhaps the most apparent, since those of ordinary skill in the art will readily appreciate that increasing transmission power leads to an increase in transmission range, assuming that as a system performance goal, a given SNR and BER are to be maintained.

In some cases, and in the context of communication systems for implantable medical devices in particular, there will be some overriding concern regarding one or more operational parameters which will guide the judgment as to which operational parameter will prevail over others during the course of the dynamic parameter adjustment in accordance with the present invention. In the foregoing description, this has been reflected in terms of the acceptable standards on operational parameters and the system performance goals defined for the link. For example, an upper limit may be imposed upon the BER of a communication system, or upon the SNR of the system. Likewise, a minimum transmission range or a maximum level of power consumption may be imposed upon the system.

In accordance with one aspect of the present invention, the performance goals of the communication system, and the standards or limits imposed upon operational parameters, may themselves be adjusted on a dynamic basis. For example, for a cardiac pacemaker patient undergoing routine follow-up care in a clinical setting, the minimum range to be maintained by the communication system can be relatively low, since it is not difficult to dispose the transceiver near the patient under these conditions. However, in an emergency situation, for example, where the patient is undergoing surgery, placing a programming head in close proximity to the implant site can be undesirable, if not impossible. Then, it would be desirable to increase the minimum transmission range to be maintained by the communication system, so that a programmer can establish telemetric communication with the patient's implanted device from a longer-than-normal distance, e.g., from bedside or even across the room. The standards for maximum levels of power consumption may also be advantageously adjusted on a dynamic, ongoing basis. For example, near the device's end-of-life power consumption is of critical concern, and it may then be desirable to impose a reduced upper limit on the amount of power consumed by the communication system.

Typically a telemetry system employing the present invention will include a plurality of performance goals applicable in conjunction with each of a variety of telemetry transmission types. In most cases it is envisioned that the performance goals will include one or more absolute requirements for a transmission to be considered acceptable. For example, in most cases a maximum error rate will be the highest priority performance goal, with acceptable error rates differing based on the telemetry type. For example, in the case of downlink of control parameters from an external programmer to an implanted device, the acceptable error rate would typically be lower than for an uplink of stored electrogram data from an implanted device to an external receiver. Similarly, the performance goal of second priority may differ between two such telemetry transmission types. For example, in the context of uplinked stored EGM segments, power conservation may be the second priority performance goal. In such case, in response to the external programmer detecting an error rate greater than the acceptable error rate, the external programmer may instruct the implanted device to decrease transmission speed and the programmer may decrease the bandwidth of the bandpass filter in its receiver circuitry. Conversely, if the error rate of the received transmission is below the acceptable error rate, the programmer may instruct the implanted device to decrease the power level of its transmission. In contrast, in conjunction with downlink of control parameters from the external programmer to the implanted device, the second priority performance goal may be increased speed of transmission. In such case, the implanted receiver on determining that the bit error rate of the received transmission is unacceptably high may instruct the external programmer to increase its transmission power level. Conversely, if the implanted device detects a sufficiently low error rate, it may instruct the external transmitter to increase its transmission speed. As an additional example, in the context of an implanted device which stores extended (e.g. 24 hour) EGM's, a relatively high maximum error rate may be acceptable, with a minimum speed of transmission and a maximum power level also required. In such case, power level reduction may have a higher priority than increasing transmission speed which in turn may have a higher priority than error rate reduction, assuming that the absolute error, power and transmission speed requirements are met. In such case, in response to detection of an excessive error rate, the external programmer may first attempt to correct the problem by instructing the implanted device to decrease transmission speed, but if this would require a transmission speed below the minimum transmission speed, thereafter instructing the implanted device to increase the transmission power level only enough to provide the required minimum error rate and speed accuracy and speed. If the power level required to meet the absolute transmission rate and accuracy requirements is above the defined maximum power level, the external programmer or monitor may instruct the physician that the distance between the programmer or monitor and the implanted device is excessive, and that the patient and programmer or monitor should be moved closer together. As yet another alternative, the physician may determine that maximum transmission range is of highest priority, with the result that one or more of the maximum error rate, minimum speed or maximum power level constraints is modified in priority or value or removed from the set of performance goals.

The above discussion assumes that during initiation of the telemetry link, initial communication between the devices may take place using a telemetry transmission protocol determined to be acceptable for transmission of control signals between the devices, as verified by return transmissions, and that this initial communication will establish the type of telemetry transmission to follow. This protocol may also be used in conjunction with adjustments of the performance parameters, as discussed above. However in many cases, feedback from the receiver to the transmitter is not required to indicate failure of the telemetry protocol in effect to meet the performance parameters. For example, in the context of the transmission of stored 24 hour electrograms discussed above, failure of the programmer to verify the accuracy of the received transmission may serve as an indicator of an unacceptable error rate. In the situation described above, the implanted device may simply then decrease the transmission rate until the minimum transmission rate is reached and thereafter increase power until either a specified maximum power level is reached or until a return transmission from the programmer indicates an acceptable error rate.

One class of RF transmission systems for which the present invention is believed to be particularly advantageous is referred to as impulse radio, a technology based upon the pulse position modulation of very low duty-cycle, ultra-wide-bandwidth RF pulses. Impulse radio (OR) pulses are processed with data encoding and pseudo-random noise encoding to smooth the energy in the frequency domain and provide channelization.

In FIG. 6, there is shown a simplified block diagram of an impulse radio transmitter 150. A pseudo-random code generator 152 perturbs the time intervals between individual clock pulses generated by a baseband clock generator 154. IR systems have been demonstrated to operate with a separation between pulses of 500-nanoseconds. Pseudo-random code generator 152 perturbs the separation of pulses by about one percent, or about 5-nanoseconds for 500-nanosecond nominal pulse separation. The resultant sequence of pulses is unique in its pulse separation, and is thus analogous to (and utilized as) a communication channel identifier.

Information is added to the baseband sequence of pseudo-randomly spaced pulses by variable delay block 156 in FIG. 6, which further perturbs the time interval between individual pulses by very small amounts, on the order of fractions of a nanosecond. The amount of perturbation is not enough to obscure the uniquely identifiable nature of the pseudo-random baseband sequence, but is sufficient to definitely impress information. The baseband pulse sequence now contains both channel identifying information and binary data to be transmitted. The encoded pulse sequence is then applied to an RF pulse generator that is coupled to a broadband RF antenna 160. Each baseband pulse triggers an RF waveform suitable for radiation from antenna 160.

In addition to providing an unique channel identification, the pseudo-random baseband code also affects the RF spectrum of the transmitted IR signal in a desirable manner. Those of ordinary skill in the art will appreciate that if the RF pulses were uniformly spaced in the transmitted signal, the RF spectrum of the transmitted signal would be occupied by regularly-spaced pulses or "comb lines." For the pseudo-randomly spaced pulses, however, the RF spectrum is more or less uniformly occupied.

In FIG. 7, there is shown a simplified block diagram of an IR receiver 170. The transmitted RF signal is received by an antenna 172. The incoming signal is correlated (i.e., multiplied and summed, as represented by multiplier block 173 in FIG. 7) with a replica of the expected signal, which is generated by a baseband clock generator 174 whose pulses are perturbed by a pseudo-random code generator 176, and an RF pulse generator 178. The correlated signal is then integrated, as represented by block 180.

If the incoming signal is not the identification of the expected channel (i.e., if the pseudo-random code generated by generator 152 in transmitter 150 is not the same as the pseudo-random code generated by generator 176 in receiver 170), then the output of integrator 180 is nearly null. On the other hand, if the incoming and expected codes are identical or nearly identical, then the output of integrator 180 will be non-zero. The output will fluctuate somewhat because the two sequences are not exactly identical—the pseudo-random code of the transmitted signal has been perturbed or modulated, slightly, by the data being transmitted. Thus, the fluctuations in the output signal from integrator 180 are used to recover the information content of the transmitted signal, after low-pass filtering in block 182. In one embodiment, the pulses in the pseudo-random baseband sequence are perturbed slightly for one data state, e.g., a binary "1," but not perturbed for the other data state, e.g., a binary "0." Thus, the correlation between the transmitted signal and the expected signal will be slightly less when a binary "1" is transmitted than when a binary "0" is transmitted. This reduced correlation is thus manifested as a decrease in the output of low-pass filter 182 for a transmitted "1" as compared with the output of low-pass filter 182 for a transmitted "0." Information content in the received signal can thus be extracted with a simple voltage comparator circuit.

A chief advantage of IR is its ability to coexist with other RF systems. IR signals are spread so widely over the RF spectrum that they are buried in ambient noise and thus mostly undetectable by conventional RF receivers. The information capacity C, in bits per second, of IR systems is given by the following equation:

$$C = BW \times \log_2(1+SNR)$$

where BW is the occupied bandwidth of the channel, and SNR is the signal-to-noise ratio. Even for very small SNR, the information capacity of an IR communication system can be made arbitrarily large by increasing the channel bandwidth.

IR systems are described in further detail in U.S. Pat. No. 4,641,317 to Fullerton, entitled "Spread Spectrum Radio Transmission System;" in U.S. Pat. No. 4,743,906 to Fullerton, entitled "Time Domain Radio Transmission System;" and in U.S. Pat. No. 4,813,057 to Fullerton, entitled "Time Domain Radio Transmission System." The Fullerton '317, '906, and '057 patents are each incorporated by reference herein in their respective entireties.

In practical implementation, IR systems are typically configured to send each bit of information multiple (up to thousands) of times, so that the fluctuations in the output of integrator 180 and low-pass filter 182 are pronounced enough to ensure reliable and accurate extraction of information content. The number of times each bit of information is transmitted is referred to as the pulse repetition factor (PRF). A operational parameter called the "integration factor" is the number of pulses integrated to determine the value of one bit.

It is believed that the integration factor is among the operational parameters of an IR system that can be advantageously monitored and dynamically adjusted in accordance with the principles of the present invention, since, by decreasing or increasing the number of pulses used to transmit each bit of information, the effective data rate is increased or decreased accordingly. Similarly, the frequency of baseband clock generators 154 and 174 in the IR transmitter and receiver of FIGS. 6 and 7, respectively, is an operational parameter of the IR system which can be adjusted up or down to achieve desired system performance goals or to maintain other operational parameters of the system within required standards or limits.

The nature of the interrelation between operational parameters and system performance goals in an IR communication system can be summarized as follows: data transmission rate is proportional to the PRF and hence inversely proportional to the integration factor; transmission range is proportional to transmission power (as previously discussed) and to the integration factor; power consumption is linearly related to the PRF. By analyzing the BER and other system performance goals, communication system 34 employing IR transmitters and receivers in accordance with the presently disclosed embodiment of the invention dynamically adapts the pulse repetition rate, integration factor, and transmission power to optimize data rate, transmission range, and power consumption.

Assuming that communication systems 34 and 100 in FIG. 5 both employ IR transmitters, a communication session between implanted device 10 and programming unit 20 transpires as follows: A communication link is established with an initially high integration factor (to maximize range) and a moderate pulse repetition rate. Once the link is established, the BER of the link is measured by error detection circuit 106. The process gain required for the desired range and error rate (including the effect of environmental noise) would be used to modulate the integration factor. The pulse repetition rate is then matched with the desired data rate and power consumption. Of course, information regarding any modulation to the pulse repetition rate must first be communicated to the receiver, so that the transmitter and receiver can stay coordinated with one another.

In situations where power consumption is of primary concern, such as for long-term ambulatory monitoring, devices with batteries nearing the end of their useful life, etc..., control circuit 112 can instruct transmitter 104 to use a lower pulse repetition rate and appropriate integration factor. In cases where high data transmission rate is a system performance goal, a higher pulse repetition rate and lower IF would be used. In cases where transmission range maximization is a system performance goal or requirement, a higher IF and higher repetition rate would be used. Optimizing the communication link's operational parameters in accordance with the principles of the present invention allows communication systems 34 and 100 to perform many functions without adding the complexity of multiple transmitters and receivers. Additionally, system performance goals and/or requirements can be dynamically adjusted during a communication session based upon data rate constraints, environmental factors, and the like. Again, any impending change in transmitter operational parameters must be preceded by a warning message to the receivers, so that the receivers will expect the change and stay coordinated with the transmitter at all times.

One benefit of the inherent channel-identifying properties of IR encoding is that multiple communication links can coexist in the same environment without risk of interchannel interference. This aspect of IR, coupled with the relatively low power requirements for IR transmitters, the frequency domain characteristics of IR transmissions, the noise immunity of IR systems, and the potential for relatively long-range of communication links, suggests that IR is particularly advantageous in the context of medical device systems. For example, it is contemplated that IR communication systems in accordance with the present invention can facilitate ambulatory monitoring of implanted device patients (due to the long range potential), as well as monitoring from outside a surgical field (again due to the long range potential), transtelephonic monitoring (due in part to the ability of the system in accordance with the present invention to automatically adapt its transmitting operational parameters—data rate, etc.—to accommodate a telephonic link), and communication with multiple devices in the same environment (for example, monitoring multiple patients in a hospital ward from a centralized monitoring station).

Since minimization of power consumption is of particular concern in the context of battery-powered body-implantable device systems, a variation upon the above-described impulse radio scheme is contemplated which takes advantage of the fact that the correlation between the received signal and the expected pseudo-random signal is less when one data state is transmitted (e.g., a transmitted "1") than when the other data state is transmitted (e.g., a transmitted "0"). In accordance with this alternative embodiment, a pseudo-random baseband code is used as described above. However, during the modulation of the pseudo-random baseband code for the purposes of introducing information content therein, pulses whose position in the pseudo-random baseband pulse stream would normally be perturbed are not transmitted at all. That is, whereas the position of a pulse would normally be perturbed in order to modulate a binary "1"into the pulse stream (in order to reduce the correlation between the received signal and the expected signal) in this alternative embodiment, that pulse is simply not transmitted. By not transmitting the pulse, the correlation, in the receiver, between the received signal and the expected signal is even less than if the pulse's position had merely been perturbed during data modulation. Pulses whose position in the pseudo-random baseband stream would not be perturbed (e.g., to modulate a binary "0" into the pulse stream) are transmitted as usual, leading to a high correlation between the received signal and the expected signal for those data bits. By not transmitting pulses corresponding to one data state, a significant reduction in power consumption can be realized.

From the foregoing detailed description of a specific embodiment of the invention, it should be apparent that a method and apparatus for implementing adaptive, optimizing communication systems, particularly well-suited, but not limited to the area of implantable medical devices, has been disclosed.

Although a specific embodiment of the invention has been described herein in some detail, this has been done solely for illustrating various aspects of the invention, and is not intended to be limiting with respect to the scope of the invention, as defined in the claims. It is contemplated that various substitutions, alterations, and/or modifications, including but not limited to those design and implementation options specifically discussed herein, may be made to the disclosed embodiment of the invention without departing from the spirit and scope of the invention, as defined by the appended claims, which follow.

What is claimed is:

1. A system comprising an impulse radio transmitter and an impulse radio receiver, wherein said impulse radio transmitter comprises means for generating a pseudo-random baseband pulse stream and means for modulating said pseudo-random baseband pulse stream with data to be transmitted, such that for a first data state, at least one pulse in said pseudo-random baseband pulse stream is not transmitted and means for transmitting said modulated pseudo-random baseband pulse stream, wherein said modulating means comprises means for deleting a pulse from said generated pseudo-random pulse stream in order to transmit said first data state.

2. A system according to claim 1, wherein said modulating means comprises means for retaining a pulse in said generated pseudo-random pulse stream in order to transmit a second data state.

3. A system according to claim 1 or claim 2 wherein said impulse radio receiver comprises;

means for generating a pseudo-random pulse stream corresponding to said pseudo-random baseband pulse stream generated by said generating means of impulse radio transmitter;

means for receiving a modulated pseudo-random pulse stream from said impulse radio transmitter;

means for correlating a received modulated pseudo-random pulse stream from said impulse radio transmitter with the pseudo-random pulse stream generated by said generating means of said impulse radio receiver; and means for recognizing lack of correlation between a pulse in the pseudo-random pulse stream generated by said generating means of said impulse radio receiver and the received modulated pseudo-random pulse stream from said impulse radio transmitter as indicative of said first data state.

4. A system according to claim 1 or claim 2 wherein said impulse radio receiver further comprises means for recognizing correlation between a pulse in the pseudo-random pulse stream generated by said generating means of said impulse radio receiver and the received modulated pseudo-random pulse stream from said impulse radio transmitter as indicative of said second data state.

* * * * *